United States Patent
Roorda

(10) Patent No.: US 8,945,180 B2
(45) Date of Patent: Feb. 3, 2015

(54) LARGE HOLE CLOSURE DEVICE

(75) Inventor: Wouter E. Roorda, Palo Alto, CA (US)

(73) Assignee: Abbott Cardiovascular Systems, Inc., Santa Clara, CA (US)

(*) Notice: Subject to any disclaimer, the term of this patent is extended or adjusted under 35 U.S.C. 154(b) by 516 days.

(21) Appl. No.: 12/877,659

(22) Filed: Sep. 8, 2010

(65) Prior Publication Data

US 2012/0059414 A1 Mar. 8, 2012

(51) Int. Cl.
*A61B 17/04* (2006.01)
*A61B 17/00* (2006.01)

(52) U.S. Cl.
CPC ......... *A61B 17/0057* (2013.01); *A61B 17/0487* (2013.01); *A61B 2017/00004* (2013.01); *A61B 2017/00663* (2013.01)
USPC .......................................... 606/232; 606/148

(58) Field of Classification Search
USPC ......... 606/232, 300, 301, 151, 153, 157, 148; 24/135 N; 411/383
See application file for complete search history.

(56) References Cited

U.S. PATENT DOCUMENTS

| | | | |
|---|---|---|---|
| 2003/0195563 A1* | 10/2003 | Foerster | 606/232 |
| 2005/0131430 A1* | 6/2005 | Ravikumar | 606/144 |
| 2005/0149120 A1* | 7/2005 | Collier et al. | 606/232 |
| 2005/0216059 A1* | 9/2005 | Bonutti et al. | 606/232 |
| 2005/0267534 A1* | 12/2005 | Bonutti et al. | 606/232 |
| 2007/0156148 A1* | 7/2007 | Fanton et al. | 606/72 |
| 2008/0086138 A1* | 4/2008 | Stone et al. | 606/72 |
| 2009/0312795 A1* | 12/2009 | Barbieri et al. | 606/232 |
| 2010/0063542 A1* | 3/2010 | van der Burg et al. | 606/232 |

* cited by examiner

*Primary Examiner* — Ashley Fishback
*Assistant Examiner* — Jing Ou
(74) *Attorney, Agent, or Firm* — Workman Nydegger; Randy Shen

(57) ABSTRACT

A closure device and system for closing openings in tissue. After placing sutures in the tissue, the sutures are clamped by the closure device to hold the sutures in place and close the opening in the tissue.

7 Claims, 3 Drawing Sheets

LARGE HOLE CLOSURE DEVICE

BACKGROUND OF THE INVENTION

1. The Field of the Invention

Embodiments of the invention relate generally to medical devices. More particularly, embodiments of the invention relate systems and methods for closing openings in tissue.

2. The Relevant Technology

Catheterization and interventional procedures, such as angioplasty or stenting, generally are performed by inserting a hollow needle through a patient's skin and tissue into the patient's vascular system. A guide wire may be advanced through the needle and into a patient's blood vessel accessed by the needle. The needle is then removed, enabling an introducer sheath to be advanced over the guide wire into the vessel, e.g., in conjunction with or subsequent to a dilator.

A catheter or other device may then be advanced through a lumen of the introducer sheath and over the guide wire into a position for performing a medical procedure. Thus, the introducer sheath may facilitate introducing various devices into the vessel, while reducing trauma to the vessel wall and/or minimizing blood loss during a procedure.

Upon completing the procedure, the devices and introducer sheath are removed, leaving a puncture site or opening in the vessel wall. Traditionally, external pressure would be applied to the puncture site until clotting and wound sealing occur; however, the patient must remain bedridden for a substantial period after clotting to ensure closure of the opening. This procedure, however, may be time consuming and expensive, requiring as much as an hour of a physician's or nurse's time. It is also uncomfortable for the patient and requires that the patient remain immobilized in the operating room, catheter lab, or holding area. In addition, a risk of hematoma exists from bleeding before hemostasis occurs.

Therefore, a need exists to close holes in tissue, particularly when the holes are large as conventional devices are not capable of closing large holes.

BRIEF SUMMARY OF THE INVENTION

Embodiments of the invention relate to systems and methods for closing opening in tissue. In one embodiment, a closure device includes an outer body that includes an opening. The closure device also includes an inner body that also has an opening formed in the inner body. The inner body and the outer body include complementary engagement mechanisms. The engagement mechanisms cooperate to close a gap between the inner body and the outer body. When in a closed position, sutures are clamped between the inner body and the outer body to hold the sutures in place and close or substantially close the opening in the tissue.

The closure device can be deployed with a holder tube. The closure device can be located in a distal end of the holder tube. After sutures are drawn through the openings in the inner body and the outer body, the inner body can be rotated or otherwise displaced or moved with a displacement member such as a rotator rod to close the gap between the inner and outer bodies and clamp the sutures. During rotation of the inner body, the openings become misaligned and the sutures are drawn into the gap. A blade formed on the rotator rod can be used to trim the sutures after the sutures are securely held in the closure device.

In another embodiment, a closure device includes an outer body that includes a bottom, an outer wall, an interior wall, a gap, and a bottom of the gap surrounded by the interior wall. The bottom of the gap has a first opening extending distally through an exterior wall of the bottom of the outer body. The gap has a first central axis and the first opening has a second central axis. The first central axis and the second central axis are offset. The outer body includes a first engagement mechanism. The closure device also includes an inner body that includes an outer wall sized and configured to fit within the interior wall of the outer body. The inner body has a bottom circumscribed by the outer wall of the inner body. The bottom of the inner body has a second opening therethrough. The inner body includes a second engagement mechanism that is complementary to the first engagement mechanism. The first engagement mechanism and the second engagement mechanism are configured to cooperate to close the gap between the bottom of the gap of the outer body and the bottom of the inner body to clamp sutures therebetween.

BRIEF DESCRIPTION OF THE DRAWINGS

To further clarify at least some of the advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. Embodiments of the invention will be described and explained with additional specificity and detail through the use of the accompanying drawings in which.

DETAILED DESCRIPTION OF THE PREFERRED EMBODIMENTS

Figure 1:
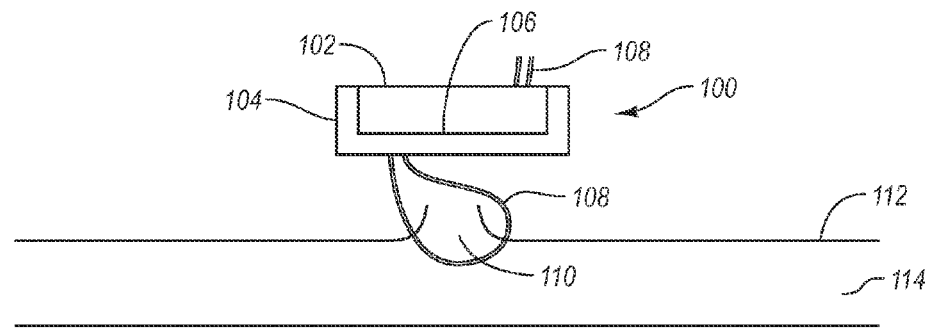
FIG. 1 shows an illustrative embodiment of a closure device used in closing an opening or hole in tissue.

Devices and methods are disclosed herein for managing access to body lumens through tissue, including management of openings in the tissue. Embodiments disclosed herein more specifically relate to closing openings or holes in body tissue. Several examples are described below in which a closure device may be deployed to close or substantially close a hole used to access a body lumen. Some embodiments may be used to close and/or substantially close openings in a blood vessel or other tissue formed during a diagnostic, therapeutic, and/or other procedure.

Embodiments of the closure devices or closure elements included therein may be made of any suitable material, including a bioabsorbable, biodegradable, or bioerodable material. Such materials may include polycaprolactone (PCL), poly(D,L-lactic acid), Poly-L-Lactic acid, poly(lactide-co-glycolide), poly(hydroxybutyrate), polyanhydrides, poly(glycolic acid, other bioabsorbable or biodegradable materials or combos thereof.

A closure device may include an inner body and an outer body. The inner body and the outer body are configured such that the inner body and outer body can move relative to each other and cooperate to aid in the closure of an opening or hole in tissue. The relative movement of the inner body and the outer body operates, for example, to clamp sutures in the closure device. More specifically, sutures can be placed in the tissue (e.g., vessel walls) surrounding an opening to a body lumen. The sutures can then be drawn into a space between the inner body and the outer body. After tightening the sutures to close the opening, the space between the inner body and the outer body is reduced or closed to clamp the sutures between the inner body and the outer body of the closure device. The closure device thus holds the sutures in place, ensuring that the opening in the tissue remains closed or substantially closed. The closure device may also include means for trimming the sutures after the sutures are secured by the closure device. For example, a movable blade, a stationery blade, and the like are examples of means for trimming the sutures. The means for trimming can be integrated with a delivery mechanism.

The following discussion refers to a vessel and to openings that may be formed in the vessel's wall during a procedure. An arteriotomy is an example of an opening in the vessel. One of skill in the art, with the benefit of the present disclosure, can appreciate that embodiments of the invention can be used to close or substantially close gaps, discontinuities, or other openings in tissue. In addition, embodiments of the invention can also be used to clamp sutures in instances that may not involve closing an opening.

The closure of a hole or opening in a vessel (or other tissue), such as an arteriotomy, formed during a procedure. The closure of the opening often requires a couple of steps. The first step includes the placement of sutures around the opening or in the walls of the vessel surrounding or proximate the opening. After the sutures are placed in the vessel, the sutures may be cinched together or tightened and then locked or held in place by the closure device. Tightening the sutures draws the walls of the vessel surrounding the opening together to substantially close the opening. Embodiments disclosed herein relate to at least one of cinching the sutures and/or clamping the sutures in place.

FIG. 1 shows an illustrative embodiment of a closure device 100 to close an opening 110 in tissue. FIG. 1 illustrates the opening 110 in tissue, such as a vessel 112. The opening 110 may often be formed during a diagnostic, therapeutic and/or other procedure to access a body lumen 114. Once the procedure is finished, the opening 110 is usually at least partially closed.

In this example, sutures 108 are used to close the opening 110. The sutures 108 are placed in the walls of the vessel 112 and in this example, the sutures 108 surround the opening 110 and are drawn through the closure device 100. In other examples, the sutures may be placed at various locations around or proximate the opening. The closure device 100, after the sutures 108 are drawn tight or cinched, can lock or hold the sutures 108 in place. The sutures 108 are locked or held in place by securing (e.g., clamping) the sutures 108 in the closure device 100.

More specifically, an inner body 102 and an outer body 104 are initially separated by a space or gap 106. The sutures 108 pass through the outer body 104 of the closure device 100 into the gap 106 and through the inner body 102 of the closure device 100. When closing the gap 106, the sutures 108 are pulled further into the gap 106. The inner body 102 and the outer body 104 cooperate to secure the sutures 108 in the gap 106.

During operation of the closure device 100, the sutures 108 are pulled into the gap 106 between the inner body 102 and the outer body 104. Once the sutures 108 are pulled into the gap 106, the gap 106 between the inner body 102 and the outer body 104 may be reduced or closed in order to clamp the sutures 108 in the closure device 100. Alternatively, the sutures 108 are pulled into the gap 106 as the gap 106 is closed. For example, rotation of the inner body 102 relative to the outer body 104 may pull the sutures 108 into the gap 106.

Figure 2A:
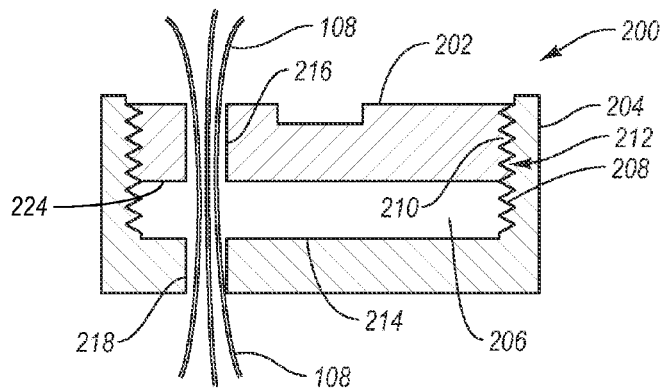
FIG. 2A shown an illustrative embodiment of a closure device for clamping sutures when closing an opening in tissue.
Figure 2B:
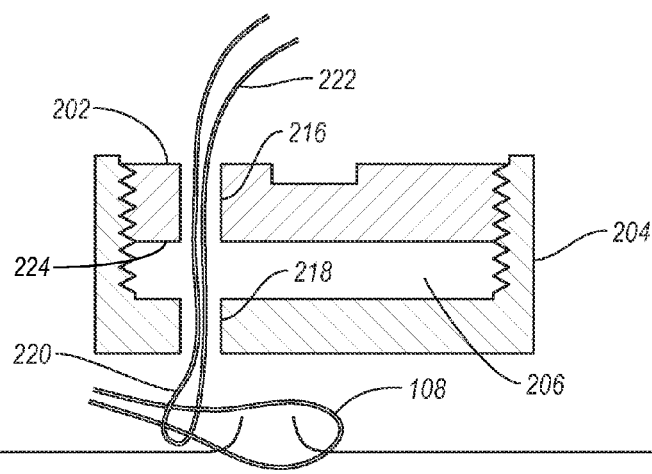
FIG. 2B shows the closure device of FIG. 2A where a snare is used to draw sutures through openings in the closure device.
Figure 2C:
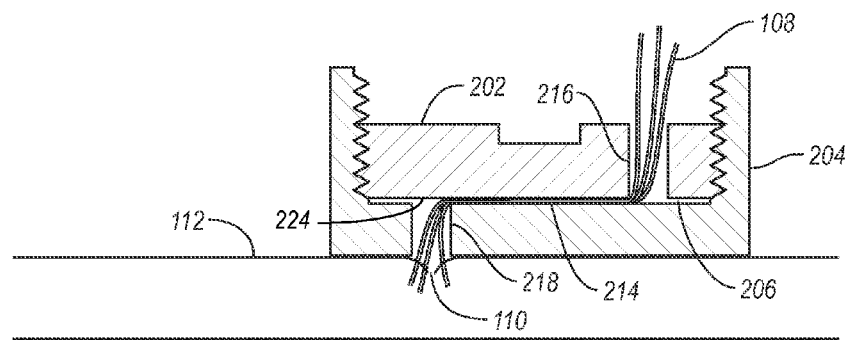
FIG. 2C shows the closure device of FIG. 2A after the sutures are drawn into the closure device and clamped to seal the opening in the tissue.

FIG. 2A shows an illustrative embodiment of a closure device 200 before the sutures 108 are clamped, FIG. 2B shows an example of a snare 222 that can draw the sutures 108 into the closure device 200, and FIG. 2C shows the closure device 200 after the closure device 200 is closed and the sutures 108 are secured in place to close the opening in the vessel. The closure device 200 may be an example of the closure device 100 shown in FIG. 1.

The closure device 200 shown in FIG. 2A includes an inner body 202 that engages with an outer body 204. A distance between the inner body 202 and the outer body 204 is defined by a gap 206. The size of the gap 206 can change because the inner body 202 and the outer body 204 may move relative to each other. An engagement mechanism 212 that connects the inner body 202 with the outer body 204 enables the inner body 202 to move relative to the outer body 204.

In this example, the engagement mechanism 212 allows the inner body 202 and/or the outer body 204 to move (e.g., lateral movement, rotational movement, or combination thereof) such that the gap 206 can be closed. In some embodiments, the inner body 202 can also be moved to open the gap 206 before and/or after the gap 206 has been closed. In fact, dimensions of the gap 206 can be increased before being closed or reduced.

Generally, the gap 206 is initially open as the closure device 200 is deployed. During operation of the closure device 200, the engagement mechanism 212 operates to close and hold the closure device 200 in a clamping or closed position (as illustrated in FIG. 2C). In the closed position, the sutures 108 are securely held or clamped between the inner body 202 and the outer body 204.

The engagement mechanism 212 includes complementary structures 208 and 210. The structure 208 is typically formed in the outer body 204 and the structure 210 is formed in the inner body 202. The complementary structures 208 and 210 may provide a threaded engagement such that the inner body 202 can rotate within the outer body 204 to close and/or open the gap 206. The complementary structures 208 and 210 may enable the gap 206 to be closed, but prevent or resist inadvertent opening of the gap 206. The engagement mechanism 212 may also include a frictional engagement. In this case the inner body 202 can be rotated and/or otherwise displaced to close the gap 206 and clamp the sutures 108. Friction between the inner body 202 and the outer body 204 keeps the sutures 108 held in the closure device 200.

Figure 2D:
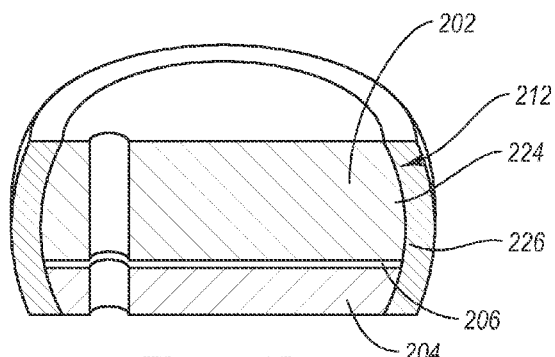
FIG. 2D shows another embodiment of an engagement mechanism of a closure device.

FIG. 2D illustrates another example of an engagement mechanism 256 for a closure device 250, which is an example of the closure device 100. In FIG. 2D, the engagement mechanism 256 includes a snap fit engagement. The inner body 252 may include an edge 258 or multiple edges that extend or protrude laterally outward from the inner body 252. The edge 258 may be a rounded protrusion or have more sharp definition. A recess 260 (or structure to accommodate multiple edges) may be formed in the outer body 254 that is configured to receive the laterally protruding edge 258. As the inner body 202 and the outer body 254 are pressed together, the outer body 254 may elastically expand to accommodate the edge 258. As the edge 258 enters the recess 260, the outer body 254 elastically contracts to securely hold the inner body 252 in the recess 226. In some instances, the inner body 252 may be rotated prior to or after snapping the inner body 252 and the outer body 254 together in order to draw the sutures 108 into the gap 262.

In another example, the outer body 254 may include projections at a distal end and a proximal end of the outer body. The inner body 252 may be held in the recess 260 by these projections. The outer body 254 is sufficiently elastic to allow the inner body 252 to be snapped into the outer body 254.

Referring back to FIG. 2A, the closure device 200 is shown prior to deployment. The inner body 202 includes an opening 216 formed therein and sized to permit passage of the sutures 108. The outer body 204 has an opening 218 formed therein that also permits passage of the sutures 108. The size and shape of the openings 216 and 218 can vary and may be selected according to the number of sutures being clamped or other considerations. For instance, the size of the openings 216 and 218 may be larger when more sutures are anticipated.

After the sutures have been placed in the wall of the vessel 112 to draw the opening 110 in the vessel 112 closed, the sutures 108 are run or drawn through the openings 216 and 218. The openings 216 and 218 are typically aligned or substantially aligned to facilitate running the sutures 108 through the openings 216 and 218 prior to deployment of the closure device 200.

FIG. 2B shows an illustrative embodiment of the closure device 200 when the sutures 108 are drawn through the openings 216 and 218. FIG. 2B illustrates a snare device 222 that includes a snare 220. The snare 220 can collect or grab the sutures 108 and draw the sutures 108 through the openings 216 and 218. One of skill in the art can appreciate that the sutures 108 can be placed in the tissue (e.g., walls of a vessel) around the opening 110 in manners well known in the art.

FIG. 2C illustrates the closure device 200 after deployment to close the opening 110. More specifically, rotation of the inner body 202 pulls the sutures 108 into the gap 206. As a greater length of the sutures 108 are drawn into the gap 206, the closure device 200 can more securely hold the sutures 108 in place. Thus, FIG. 2C illustrates that the sutures 108 have been drawn into the gap 206 by rotation of the inner body 202 relative to the outer body 204.

The opening 110 is substantially closed or reduced in size by cinching or tightening the sutures 108, which can be achieved by pulling on the sutures 108 in a proximal direction or in another manner well known in the art. Once the sutures 108 are tightened, the gap 206 is closed to clamp the sutures 108 between the inner body 202 and the outer body 204. Once the closure device 200 is in the clamping position, the sutures 108 are held and the opening 110 is closed or substantially closed and remains closed after the sutures 108 are trimmed. In one example, the closure device 200 clamps the sutures 108 when the inner body 202 moves towards the bottom 214 of the outer body 204 to close the gap 206.

In one example, the gap 206 is closed by rotating the inner body 202 relative to the outer body 204. The engagement mechanism 212 is configured to close the gap 206 as the inner body 202 rotates. In other words, the engagement mechanism 212 moves an interior suture engaging bottom 224 of the inner body 202 towards the interior suture engaging bottom 214 of the outer body 204 as the inner body 202 rotates. When the engagement mechanism 212 includes a threaded engagement, the inner body 202 can be screwed to close the gap 206. In one example, the closure of the closure device 200 is completed when the sutures 108 are sufficiently clamped.

Generally, the opening 216 is not aligned with the opening 218 after the sutures 108 are clamped or held securely in the closure device 200 or when the closure device 200 is in a clamping position. As previously stated, the openings 216 and 218 are usually aligned as the sutures 108 are drawn into the closure device 200. The closure device 200 may then be configured such that clamping is achieved after the inner body 202 rotates approximately 180 degrees in one example or some other rotation that results in clamping of the sutures 108 when the openings 216 and 218 are no longer aligned. Half a rotation (or one and a half rotations, etc.) draws the sutures 108 into the gap 206 to maximize the amount of suture in the gap 108 that is clamped by the inner body 202 and the outer body 204. The engagement mechanism 212 may be configured to close the gap 206 after half a rotation.

During closure of the opening 110 in the vessel 112, the closure device 200, and more specifically the outer body 204, may be adjacent and/or touching the vessel 112 or be adjacent the opening 110. In addition, the opening 218 may be substantially aligned with the opening 110 after the sutures 108 are securely held in the closure device 200. Further, the sutures 108 are typically drawn tight such that the walls of the opening 110 are brought together to close the opening 110 before clamping or securing the sutures 108 in the closure device 200. The closure device 200 can be removed by snipping one of the sutures 108 at a location between the vessel 112 and the closure device 200. When the appropriate sutures are snipped, the sutures 108 can be withdrawn and the closure device 200 removed.

Figure 3A:
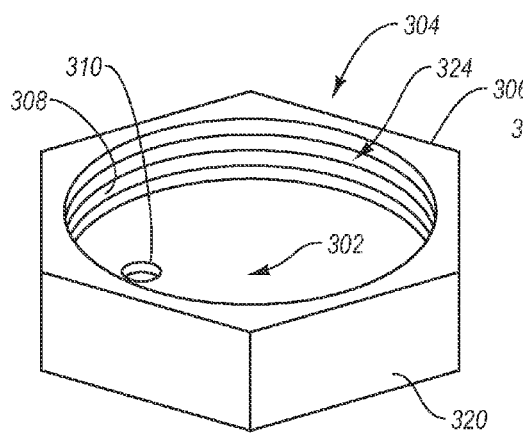
FIG. 3A shows an illustrative top perspective view of an outer body of an embodiment of a closure device.
Figure 3B:
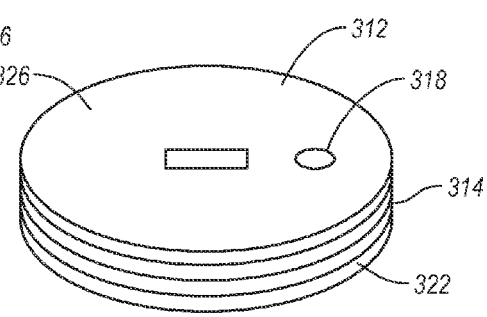
FIG. 3B shows an illustrative top perspective view of an embodiment of an inner body of a closure device.

FIG. 3A illustrates a top perspective view of an outer body 304 of a closure device and FIG. 3B illustrates a top perspective view of an inner body 312 of the closure device. FIG. 3A illustrates an outer body 304, which is an example of the outer body 104 or the outer body 204. The outer body 304 includes an opening 310 that is non-centric in this example relative to an axis 312. Alternatively, the opening 310 may be centric as long as the opening in the inner body is non-centric such that the sutures can be drawn into the gap or space between the inner and outer body and clamped in place as described herein. The shape of the opening 310 can also vary.

A height of the outer body may be between 0.5 and 5 mm, preferably between 1 and 3 mm. A width of the outer body may be between 1 and 10 mm, preferable between 2 and 4 mm. One of skill in the art can appreciate that the dimensions are provided by way of example only and not limitation. Other dimensions inside and/or outside of these example ranges are contemplated within the scope of the invention.

FIG. 3A also shows a perimeter 306 of the outer body 304. The perimeter 306 is typically configured such that the outer body 304 can be held in place when the inner body is rotated or moved to clamp the sutures. By way of example only, the perimeter 306 may be hexagonal, square, or any other polygonal shape or an irregular, symmetrical or asymmetrical shape. In addition, the various sides 320 of the perimeter 306 may be of different lengths. The interior wall 308 is typically round to enable rotation of the inner body, although other configurations are contemplated. The engagement mechanism (e.g., threads, clip, snap, projections) are formed in the interior wall 308.

FIG. 3B shows a top perspective view of an inner body 302, which may be an example of the inner body 102 or the inner body 202. The inner body 302 has an outer wall 314 that is configured with an engagement mechanism 322 (e.g., threads) to cooperate or engage with a corresponding engagement mechanism 324 formed in the interior wall 308 of the outer body 304. The complementary portion of the engagement mechanism is formed in the outer wall 314.

The opening 318 is non-centrically located in the inner body 302 in FIG. 3B. In one example, both the opening 318 and the opening 310 are non-centric and located, respectively, in the inner body 302 and the outer body 304 such that the openings 318 and 310 can be aligned to facilitate drawing the sutures through the openings 318 and 310 prior to deployment of the closure device. After rotation of the inner body 302 during deployment, the openings 318 and 310 become un-aligned such that the sutures become clamped as described herein.

The inner body 302 also includes a displacement mechanism, such as a slot 316 formed in a top surface 326. The slot 316 can be engaged in order to rotate the inner body 302 and deploy the closure device. Rotation of the inner body 302 using the slot 316 pulls the sutures 108 into the gap and clamps or secures the sutures in the closure device. The slot 316 can be of any shape, depth, and/or be otherwise configured to enable rotation of the inner body 302. The sutures can be pulled into the gap between the inner body and the outer body from either below the closure device and/or from above the closure device.

Figure 4A:
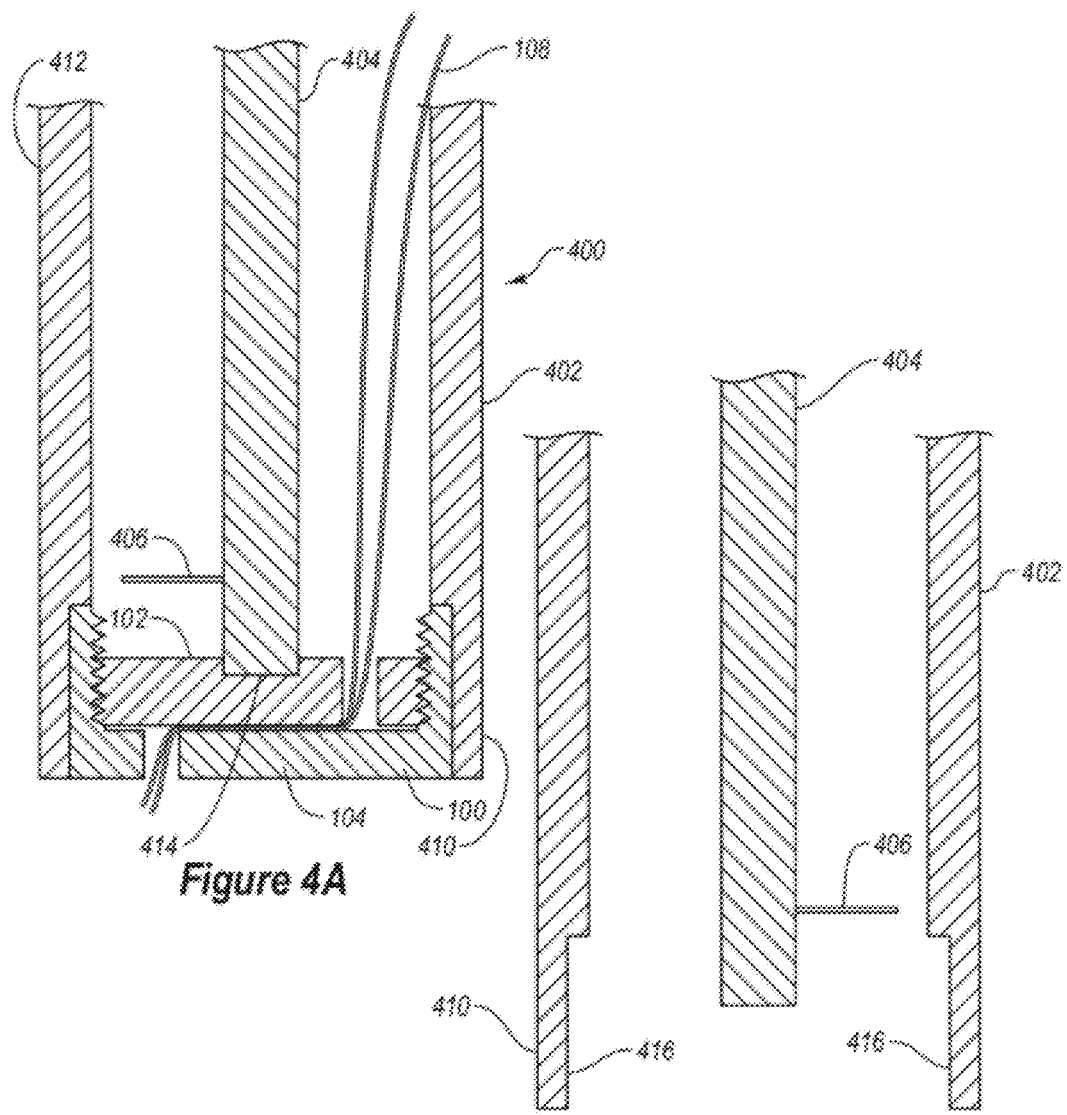
FIG. 4A shows an illustrative embodiment of a closure system that deploys a closure device.

FIG. 4A illustrates a closure system 400 for deploying, by way of example, the closure device 100. The closure system 400 includes the closure device 100 (see FIG. 1) that is held in a distal end 410 of a holder tube 402. The distal end 410 of the holder tube 402 is configured to hold the closure device 100 such that the outer body 104 of the closure device 100 does not move when the inner body 102 of the closure device 100 is rotated or otherwise repositioned to clamp or secure the sutures 108 within the closure device 100. The distal end 410 of the holder tube 402 may be non-circular to prevent the outer body of the closure device 100, which may also have a non-circular perimeter as shown in FIG. 3A, from rotating. For example, the distal end 410 may define a hexagonal opening (or other shape) to receive and hold a similarly shaped outer body, such as the outer body 304 shown in FIG. 3A. The closure device may be held in the distal end 410 by friction such that the closure device 100 does not inadvertently fall out of the holder tube 402.

The holder tube 402 is thus shaped to hold the outer body 104 of the closure device to allow the inner body 102 of the closure device 100 to be rotated (or otherwise repositioned) relative to the outer body 104 in order to clamp the sutures 108. For example, the distal end 410 may have a recess 416 (see FIG. 4B) formed therein that is sized and shaped to receive the closure device 100. The perimeter of the recess 416, for example, matches the perimeter of the outer body 104. The recess 416 may also have a depth to match the depth of the closure device 100. Other configurations, such as tabs and slots, or other rotational features may also be includes.

Rotation of the inner body 102 can be performed with a rotator rod 404. The rotator rod 404 engages displacement mechanism such as a slot 414 (an example of the slot 316) formed in a top of the inner body 102. The rotator rod 404 and the slot 414 are mutually configured to engage to facilitate rotation of the inner body 102 to clamp or secure the sutures 108. The rotator rod 404 may extend out of the holder tube 402 such that a user can grasp the rotator rod 404 and move the rotator rod 404 distally and/or proximally and/or rotate the rotator rod 404. A proximal end of the rotator rod and/or a proximal end of the holder tube 402 may be configured for grasping by a user. In addition, the sutures 108 may extend out of the holder tube 402 such that the sutures 108 can be grasped and tightened. For example, a user may pull proximally on the sutures 108 to tighten the sutures. The closure device 100 can then be closed to clamp the sutures 108. The holder tube 402 can push the outer body 104 distally while the sutures 108 are pulled proximally. This positions the closure device 100 appropriately near the opening in the vessel and tightens the sutures 108 at the same time. Often, the outer body 104 will be in contact with the vessel or sufficiently close such that the sutures 108 do not slacken or become loose after deployment of the closure device 100.

Figure 4B:
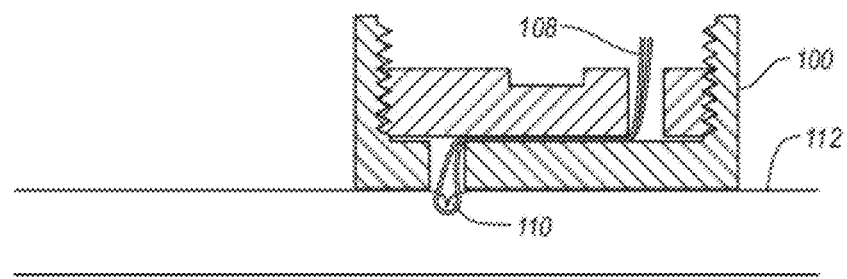
FIG. 4B shows an illustrative embodiment of the closure system in FIG. 4A after the closure device is deployed.

FIG. 4B shows an illustrative embodiment of the closure system 400 after deployment of the closure device 100 to close or substantially close the opening 110 in the vessel 112. After the sutures 108 are clamped or secured in the closure device 100 as previously described, the sutures 108 can be trimmed. In this example, the rotator rod 404 includes a blade 406 extending from the rotator rod 404. The blade 406 can be rotated to trim the sutures 108. In one example, the rotator rod 404 is disengaged from the slot 414 before the sutures 108 are trimmed as illustrated in FIG. 4B. After disengaging the rotator rod 404, the rotator rod 404 can be twisted to trim the sutures 108. Alternatively, the sutures 108 can be pulled against the blade 406, for example, by wrapping the sutures 108 around the rotator rod 404 and pulling on the sutures 108 to trim the sutures 108.

FIG. 4B also illustrates that the distal end 410 of the holder tube may include the recess 416 to accommodate at least a portion of the closure device 100. The closure device 100 may be positioned in the recess 416 such that the bottom surface of the closure device 100 is substantially flush with the bottom of the holder tube 402. During deployment, the closure device 100 may be held in the recess 416 such that the closure device 100 is held in place while the sutures are drawn through the openings formed in the closure device 100. The sutures 108 can be drawn through the openings (e.g., through both the outer body and the inner body) in the closure device 100 when convenient. After the sutures 108 are drawn into the closure device 100, the closure device 100 is positioned against the opening 110 and the sutures 108 are tightened and the closure device 100 is closed to clamp the sutures 108.

After the sutures 108 are clamped between the inner body 102 and the outer body 104, the holder tube 402 can be extracted or withdrawn, leaving the closure device 100 held in place adjacent the opening 110. Because the sutures 108 are secured in the closure device 100, the closure device 100 remains in place when the holder tube 402 is removed. The force applied by the closure device 100 to the sutures 108 may be sufficient to cause the closure device 100 to be removed from the holder tube 402 during removal of the holder tube. The rotator rod 404 can also be used, in one example, to aid in extracting the holder tube 402 or for pushing the closure device 100 out of the recess 416. Because the sutures 108 are clamped, the sutures 108 that have been placed in the vessel 112 to draw the opening 110 closed may keep the opening 110 closed.

The closure devices disclosed herein (can be comprised of a variety of known suitable materials, including stainless steel, silver, platinum, tantalum, palladium, nickel, titanium, nitinol, nitinol alloys having tertiary materials, niobium-tantalum alloys optionally doped with a tertiary material, cobalt-chromium alloys, or other known biocompatible materials. Such biocompatible materials can include a suitable biocompatible polymer in addition to or in place of a suitable metal. A device or member can include biodegradable, bioerodable, or bioabsorbable materials.

In one embodiment, the closure device or other medical device can be made at least in part of a high strength, low modulus metal alloy comprising niobium, tantalum, and at least one element selected from the group consisting of zirconium, tungsten, and molybdenum. The materials composing the medical devices or members according to the present invention may provide superior characteristics with regard to biocompatibility, radio-opacity and MRI compatibility.

Furthermore, the closure device body or other medical device, including the closure device, can be formed from a ceramic material. In one aspect, the ceramic can be a biocompatible ceramic that optionally can be porous. Examples of suitable ceramic materials include hydroxylapatite, mullite, crystalline oxides, non-crystalline oxides, carbides, nitrides, silicides, borides, phosphides, sulfides, tellurides, selenides, aluminum oxide, silicon oxide, titanium oxide, zirconium oxide, alumina-zirconia, silicon carbide, titanium carbide, titanium boride, aluminum nitride, silicon nitride, ferrites, iron sulfide, and the like. Optionally, the ceramic can be provided as sinterable particles that are sintered into the shape of a closure device or layer thereof.

Moreover, the closure device body or other medical device can include a radiopaque material to increase visibility during placement. Optionally, the radiopaque material can be a layer or coating any portion of the device or member. The radiopaque materials can be platinum, tungsten, silver, stainless steel, gold, tantalum, bismuth, barium sulfate, or a similar material.

It is further contemplated that the external surface and/or internal surface of the devices or members (e.g., exterior and luminal surfaces) as well as the entire body can be coated with another material having a composition different from the primary material. The use of a different material to coat the surfaces can be beneficial for imparting additional properties to the device or member, such as providing radiopaque characteristics, drug-reservoirs, and improved biocompatibility.

The closure device can also be formed from biocompatible polymeric materials that can include a suitable hydrogel, hydrophilic polymer, hydrophobic polymer, biodegradable polymer, bioabsorbable polymer, and monomers thereof. Examples of such polymers can include nylons, poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, ethylenevinylalcohol copolymers (EVAL), propylenevinylalcohol copolymers, polyvinylpyrrolidone (PVP), combinations thereof, polymers having monomers thereof, or the like.

Accordingly, embodiments of the invention can include or be coated with a drug or beneficial agent, for example an antibiotic, to improve the use of the closure device.

The invention is susceptible to various modifications and alternative means, and specific examples thereof have been shown by way of example in the drawings and are herein described in detail. It should be understood, however, that the invention is not to be limited to the particular devices or methods disclosed, but to the contrary; the invention is to cover all modifications, equivalents, and alternatives falling within the spirit and scope of the claims.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A closure device for closing an opening, the closure device comprising:
   an outer body having an exterior bottom, an outer wall, an interior wall, and an interior suture engaging bottom, the interior suture engaging bottom having a first opening extending distally through an exterior wall of the bottom of the outer body, the outer body having a first central axis and the first opening having a second central axis, the first central axis and the second central axis being offset, the outer body including a first engagement mechanism; and
   an inner body having an outer wall sized and configured to engage with the interior wall of the outer body, the inner body having a suture engaging bottom circumscribed by the inner wall of the outer body, the suture engaging bottom of the inner body having a second opening therethrough, the inner body including a second engagement mechanism that is complementary to the first engagement mechanism, wherein the first engagement mechanism includes first threads and the second engagement mechanism includes second threads, wherein the first engagement mechanism and the second engagement mechanism are configured to cooperate to close a gap between the interior suture engaging bottom of the outer body and the suture engaging bottom of the inner body to clamp sutures therebetween, wherein the top of the inner body is disposed below the top of the outer body when the inner body and the outer body are in a closed position with the inner body clamping sutures between the interior suture engaging bottom of the outer body and the suture engaging bottom of the inner body, wherein the inner body is threaded inside the outer body with the first opening and the second opening substantially aligned prior to deployment of the closure device; and wherein the first opening and the second opening are misaligned to lock the sutures after deployment of the closure device.

2. The closure device of claim 1, wherein the first engagement mechanism and the second engagement mechanism enable the inner body to rotate within the outer body to close the gap.

3. The closure device of claim 1, wherein the first opening is non-centrically located in the outer body and wherein the second opening is non-centrically located in the inner body.

4. The closure device of claim 1, the inner body comprises a slot on a top surface, wherein the slot is configured to engage with a rotator rod to rotate the inner body.

5. The closure device of claim 1, wherein the first opening and the second opening receive sutures and wherein rotation of the inner body pulls the sutures into the gap, wherein the sutures are clamped between when the inner body and the outer body are in a closed position.

6. The closure device of claim 1, wherein the gap is bounded by the interior wall of the outer body, the interior suture engaging bottom of the outer body and the suture engaging bottom of the inner body.

7. The closure device of claim 1, wherein sides of the gap are formed by the interior wall of the outer body.

* * * * *